(12) United States Patent
Levy et al.

(10) Patent No.: US 8,197,515 B2
(45) Date of Patent: Jun. 12, 2012

(54) CROSS-CONNECTOR ASSEMBLY

(75) Inventors: Mark M. Levy, Raanana (IL); Eyal Zylberberg, Kfar Yona (IL); Yair Spanier, Pardes Hanna (IL); Amnon Yadin, Kfar Vitkin (IL)

(73) Assignee: Expanding Orthopedics Inc., Memphis, TN (US)

( * ) Notice: Subject to any disclaimer, the term of this patent is extended or adjusted under 35 U.S.C. 154(b) by 310 days.

(21) Appl. No.: 12/032,721

(22) Filed: Feb. 18, 2008

(65) Prior Publication Data
US 2009/0210007 A1 Aug. 20, 2009

(51) Int. Cl.
*A61B 17/70* (2006.01)
(52) U.S. Cl. ......... 606/250; 606/251; 606/252; 606/278
(58) Field of Classification Search .......... 606/250–253, 606/260, 151, 264–279, 300–321, 246
See application file for complete search history.

(56) References Cited

U.S. PATENT DOCUMENTS

| 7,485,132 B1 * | 2/2009 | McBride et al. ............... 606/250 |
| 7,635,380 B2 * | 12/2009 | Zucherman et al. .......... 606/267 |
| 2005/0228377 A1 * | 10/2005 | Chao et al. ....................... 606/61 |
| 2006/0229616 A1 | 10/2006 | Albert et al. |
| 2008/0082112 A1 * | 4/2008 | Lawton et al. ................. 606/151 |

FOREIGN PATENT DOCUMENTS

| DE | 10246418 | 4/2004 |
| WO | 99/09901 | 3/1999 |
| WO | 03/068087 | 8/2003 |
| WO | 2007/121128 | 10/2007 |

* cited by examiner

*Primary Examiner* — Eduardo C Robert
*Assistant Examiner* — Christina Negrelli
(74) *Attorney, Agent, or Firm* — Dekel Patent Ltd; David Klein (57) ABSTRACT

An assembly including a connector element including a receptacle from which extends a neck, a lug element sized to fit in the receptacle of the connector element, ears pivotally connected to the lug element, and a mechanical fastener that fastens the connector element together with the lug element, thereby causing the ears to pivot and grip a connector rod placed between the ears.

14 Claims, 8 Drawing Sheets

CROSS-CONNECTOR ASSEMBLY

FIELD OF THE INVENTION

The present invention relates generally to anchoring structures for orthopedic devices, and particularly to a connector assembly for connecting rods and the like to bone anchoring elements, such as pedicle screws.

BACKGROUND OF THE INVENTION

Many spinal fixation systems are found in the prior art for fixing connecting rods and the like to pedicle screws. Some systems have a disadvantage in that the rod must be bent after coupling to the pedicle screw because of anatomical considerations. Some systems attempt to solve this problem with different kinds of connectors that secure the rod to a polyaxial pedicle screw head and permit spatial adjustments before locking the rod in place. In order to achieve additional stability of the fixation system, especially when more levels or screws are added to the structure, cross bars or connectors are installed linking the rods of both sides of the vertebra. Such cross connectors add rigidity to the system but increase stress in the rod contact area. To adapt to anatomical constraints, the cross connectors should be fixable at different lengths and angles to fit the position of the anchoring elements attached to the bones. Nevertheless, no design is free of problems and there is still a need for a connector that is "user-friendly" and permits adjustments before locking the rod in place.

SUMMARY OF THE INVENTION

The present invention seeks to provide an improved connector for connecting rods and the like to bone anchoring elements, such as pedicle screws, as is described more in detail hereinbelow. The connector of the invention permits rotational and translational adjustments before locking the rod in place.

There is thus provided in accordance with an embodiment of the present invention an assembly including a connector element including a receptacle from which extends a neck, a lug element sized to fit in the receptacle of the connector element, ears pivotally connected to the lug element, and a mechanical fastener that fastens the connector element together with the lug element, thereby causing the ears to pivot and grip a connector rod placed between the ears.

A transverse connector element may be connected to the connector element in a telescoping manner. For example, the transverse connector element includes a receptacle from which extends a transverse rod that is received in the neck of the connector element in a telescoping manner.

In accordance with an embodiment of the present invention another lug element is sized to fit in the receptacle of the transverse connector element, wherein ears are pivotally connected to the other lug element, and another mechanical fastener fastens the transverse connector element together with the other lug element, thereby causing the ears to pivot and grip another connector rod placed between the ears. The connector rods are connected to bone anchoring elements.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Reference is now made to FIGS. 1-4, which illustrate a cross-connector assembly 10 for a bone anchoring element, constructed and operative in accordance with an embodiment of the present invention.

The cross-connector assembly 10 may be constructed of any suitable, medically safe material, such as but not limited to, stainless steel alloy (e.g., AISI 316L), titanium or titanium alloy or chrome cobalt alloy, PEEK, shape memory alloys or polymers, or any combination thereof. Different parts of cross-connector assembly 10 may be constructed of different materials with different resilience or hardness, or of the same material but treated to have different resilience or hardness.

In a non-limiting embodiment of the invention, cross-connector assembly 10 includes a connector element 12 that cooperates with a lug element 14 and pivoting ears 16 for gripping a connecting rod (or other bone anchoring element) 18. The connector element 12 is connected to a transverse connector element 20 in a telescoping manner. Transverse connector element 20 also cooperates with another lug element 14 and pivoting ears 16 for gripping another connecting rod 18. The structure of connector element 12, lug element 14 and transverse connector element 20 will now be described and afterwards the assembly of the parts will be described.

Figure 8A:
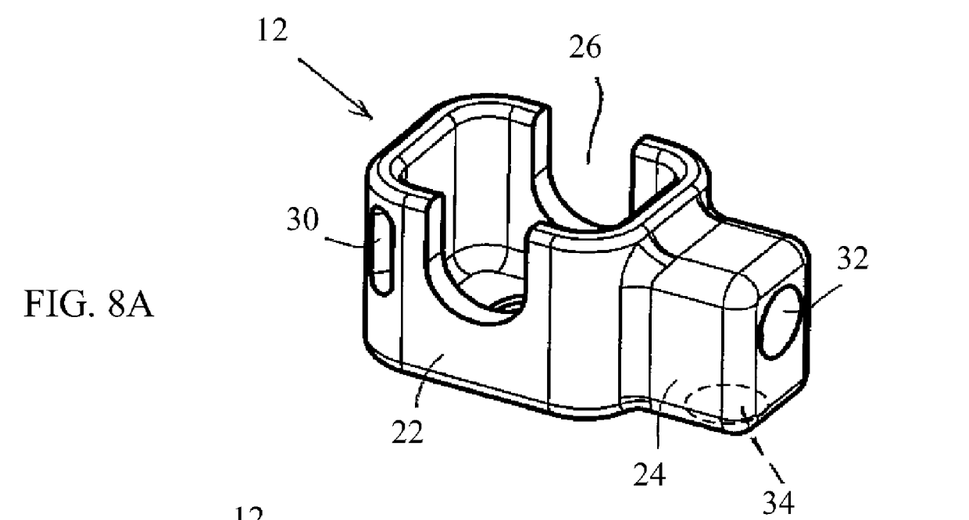
FIGS. 8A and 8B are two different simplified pictorial illustrations of a connector element that is fastened together with a lug element for gripping a connecting rod, in accordance with an embodiment of the present invention.
Figure 8B:
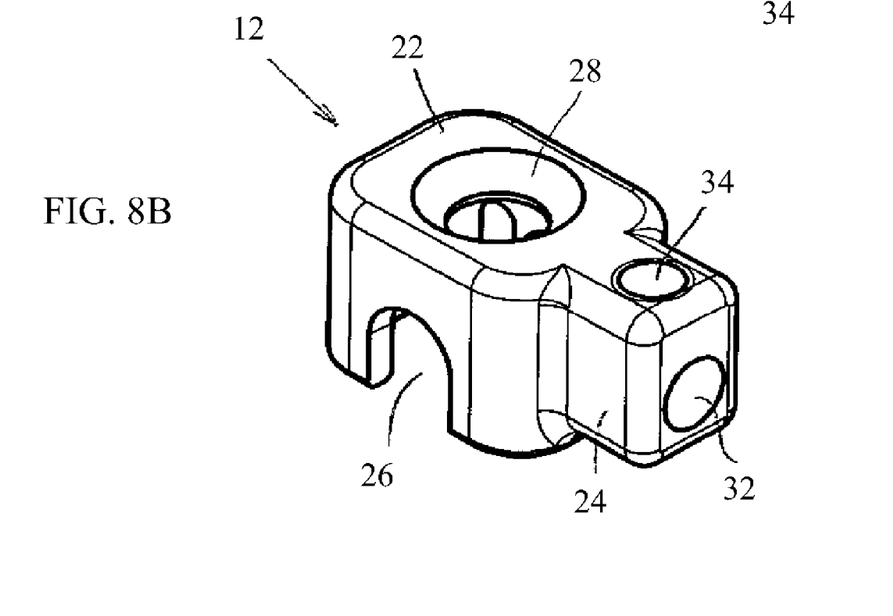

Reference is now made to FIGS. 8A and 8B, which illustrate connector element 12, in accordance with an embodiment of the present invention. Connector element 12 includes a receptacle 22 from which extends a neck 24, preferably of smaller cross-sectional shape than receptacle 22. Receptacle 22 may be prismatic or rounded in shape and is formed with aligned U-shaped apertures 26 on opposite side walls thereof, a tapped hole 28 on a top portion thereof, and an elongate oval hole 30 on a rounded corner thereof. Neck 24 is formed with a (typically blind) hole 32 at an end thereof and a tapped hole 34 on a top portion thereof.

Figures 9A, 9B:
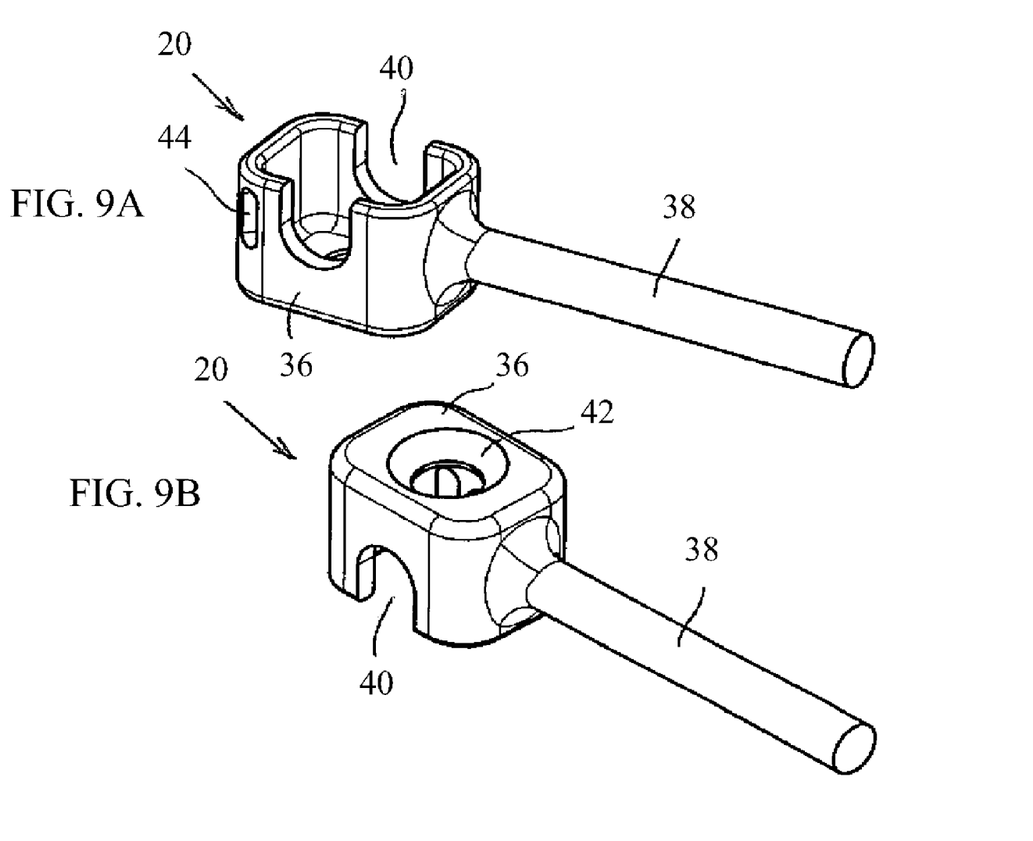
FIGS. 9A and 9B are two different simplified pictorial illustrations of a transverse connector element that is fastened together with the lug element for gripping the connecting rod, in accordance with an embodiment of the present invention.

Reference is now made to FIGS. 9A and 9B, which illustrate transverse connector element 20, in accordance with an embodiment of the present invention. Transverse connector element 20 includes a receptacle 36 from which extends a transverse rod 38, preferably of smaller cross-sectional shape than receptacle 36. Receptacle 36 may be prismatic or rounded in shape and is formed with aligned U-shaped apertures 40 on opposite side walls thereof, a tapped hole 42 on a top portion thereof, and an elongate oval hole 44 on a rounded corner thereof. Transverse rod 38 is sized to fit into blind hole 32 of connector element 12.

Figures 10A, 10B:
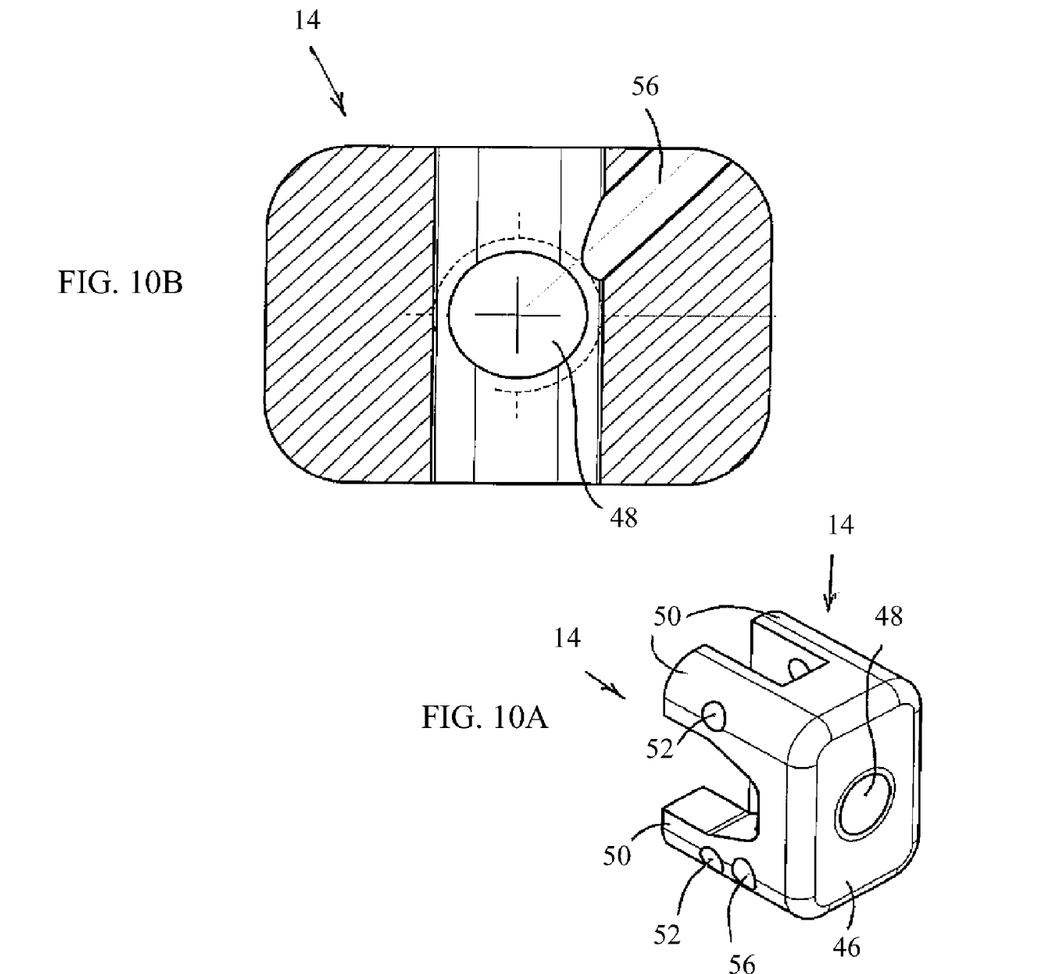
FIGS. 10A-10B are simplified pictorial and sectional illustrations, respectively, of the lug element, to which pivoting ears are attached for gripping the connecting rod in accordance with an embodiment of the present invention.

Reference is now made to FIGS. 10A-10B, which illustrate lug element 14 in accordance with an embodiment of the present invention. Lug element 14 resembles a miniature footstool and is sized to fit in the receptacle 22 of connector element 12 and the receptacle 36 of transverse connector element 20. The body of lug element 14 includes a top surface 46 formed with a tapped hole 48. Four legs 50 (that is, two pairs of legs) extend from top surface 46. Each pair of legs 50 is formed with holes 52 for pivotally pinning thereto the ears 16 with a pin 54 (not shown here but seen in FIG. 3), the purpose of which is explained further below. An angled hole 56 is formed through the side of lug element 14 near one of the legs 50 and goes through to the bottom of tapped hole 48.

The cross-connector assembly 10 may be assembled as follows, with reference again to FIGS. 1-4.

Two ears 16 are pinned to each lug element 14. One connector rod 18 is placed between the ears 16 of lug element 14. Lug element 14 is placed in receptacle 22 of connector element 12 so that the tapped hole 48 of lug element 14 is aligned with the tapped hole 28 of connector element 12. A mechanical fastener (e.g., screw) 58 is screwed into the tapped holes 28 and 48. This pulls lug element 14 towards the top portion of connector element 12, which causes the ears 16 to abut against the inner side walls of connector element 12. This causes the ears 16 to pivot about pins 54 and wrap against connector rod 18. Thus, ears 16 grip connector rod 18 tightly due to the tightening of lug element 14 with connector element 12. A pin 59 may be placed though elongate oval hole 30 into angled hole 56 to further fasten lug element 14 with connector element 12.

Similarly, another connector rod 18 is placed between the ears 16 of another lug element 14, which is placed in receptacle 36 of transverse connector element 20, so that the tapped hole 48 of lug element 14 is aligned with the tapped hole 42 of transverse connector element 20. Another screw 58 is screwed into the tapped holes 42 and 48. This pulls lug element 14 towards the top portion of transverse connector element 20, which causes the ears 16 to abut against the inner side walls of transverse connector element 20. This causes the ears 16 to pivot about pins 54 and wrap against connector rod 18. Thus, ears 16 grip connector rod 18 tightly due to the tightening of lug element 14 with transverse connector element 20. Another pin 59 may be placed though elongate oval hole 44 into angled hole 56 to further fasten lug element 14 with transverse connector element 20.

Figure 1:
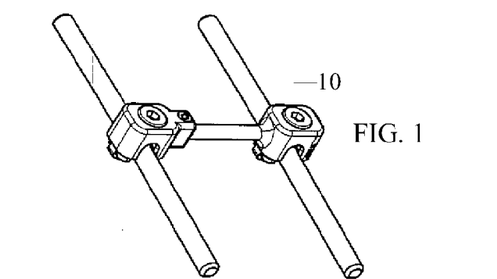
FIGS. 1, 2, 3 and 4 are simplified pictorial, side-view, sectional and front-view illustrations, respectively, of a cross-connector assembly for a bone anchoring element, constructed and operative in accordance with an embodiment of the present invention.
Figure 2:
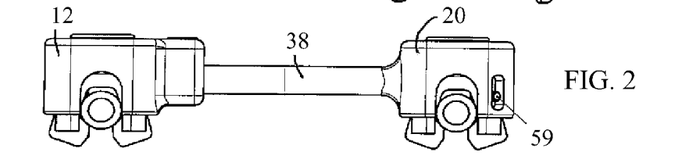
Figure 3:
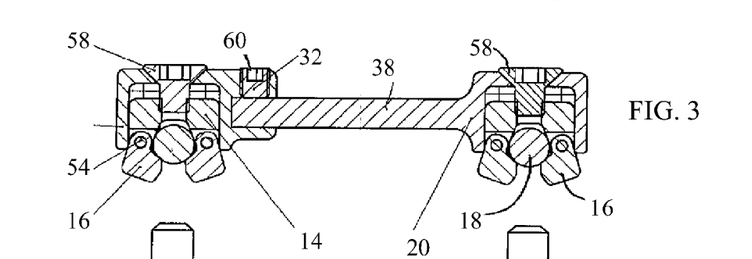
Figure 4:
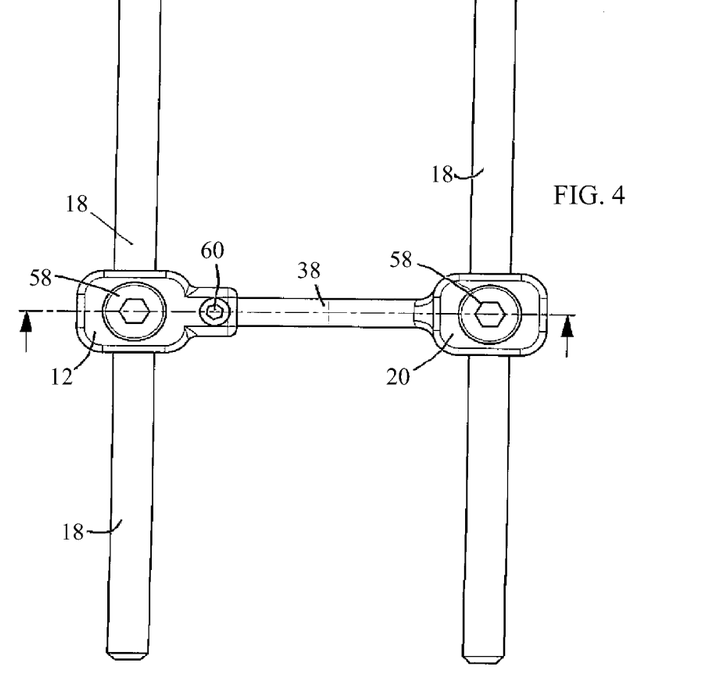
Figure 5:
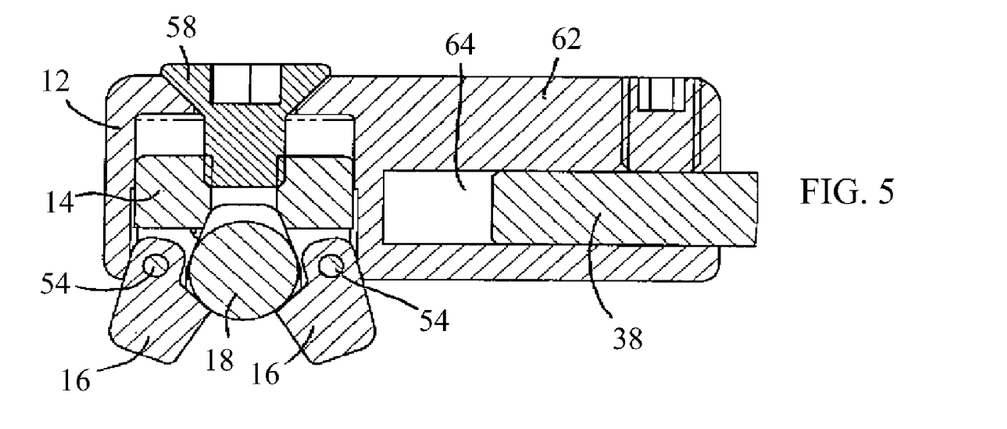
FIGS. 5, 6 and 7 are simplified first sectional, front-view and second sectional illustrations, respectively, of a cross-connector assembly similar to the embodiment of FIGS. 1-4, with a longer telescoping section.
Figure 6:
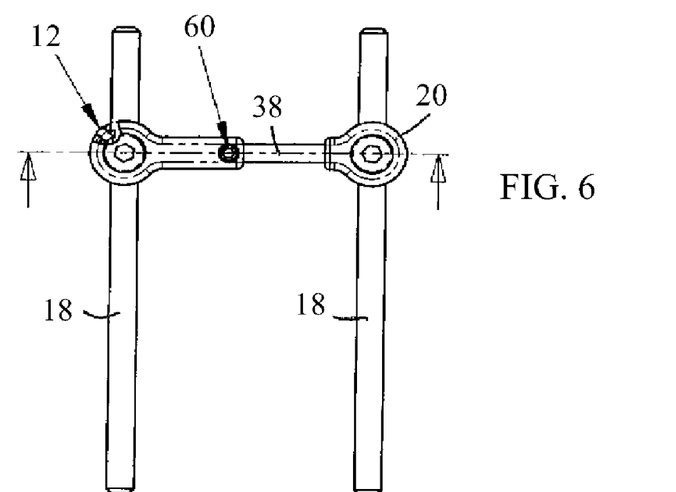
Figure 7:
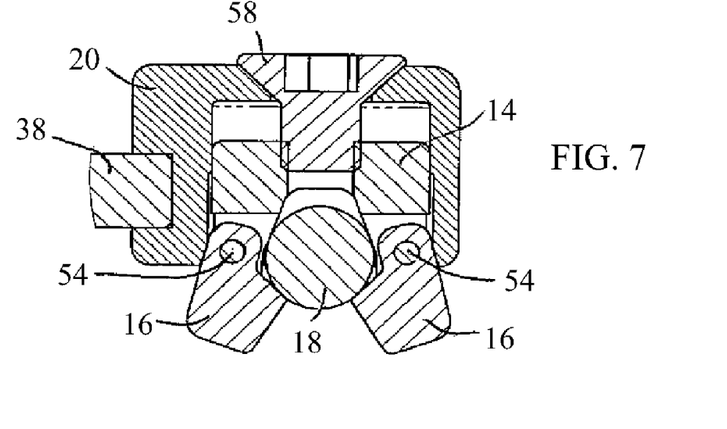

The transverse rod 38 of transverse connector element 20 is placed in the blind hole 32 of neck 24 of connector element 12. A mechanical fastener (e.g., screw) 60 is then tightened against transverse rod 38 through tapped hole 34 of neck 24. It is appreciated that transverse rod 38 may be positioned telescopically at any desired position with respect to connector element 12 within the limits of the length of neck 24. FIGS. 5-7 show another embodiment with a longer neck 62 and longer blind hole 64 (like elements being designated by like numerals). Neck 24 or longer neck 62 can have partially open sides to allow angular freedom of the transverse rod 38 before locking (not shown).

Figure 11:
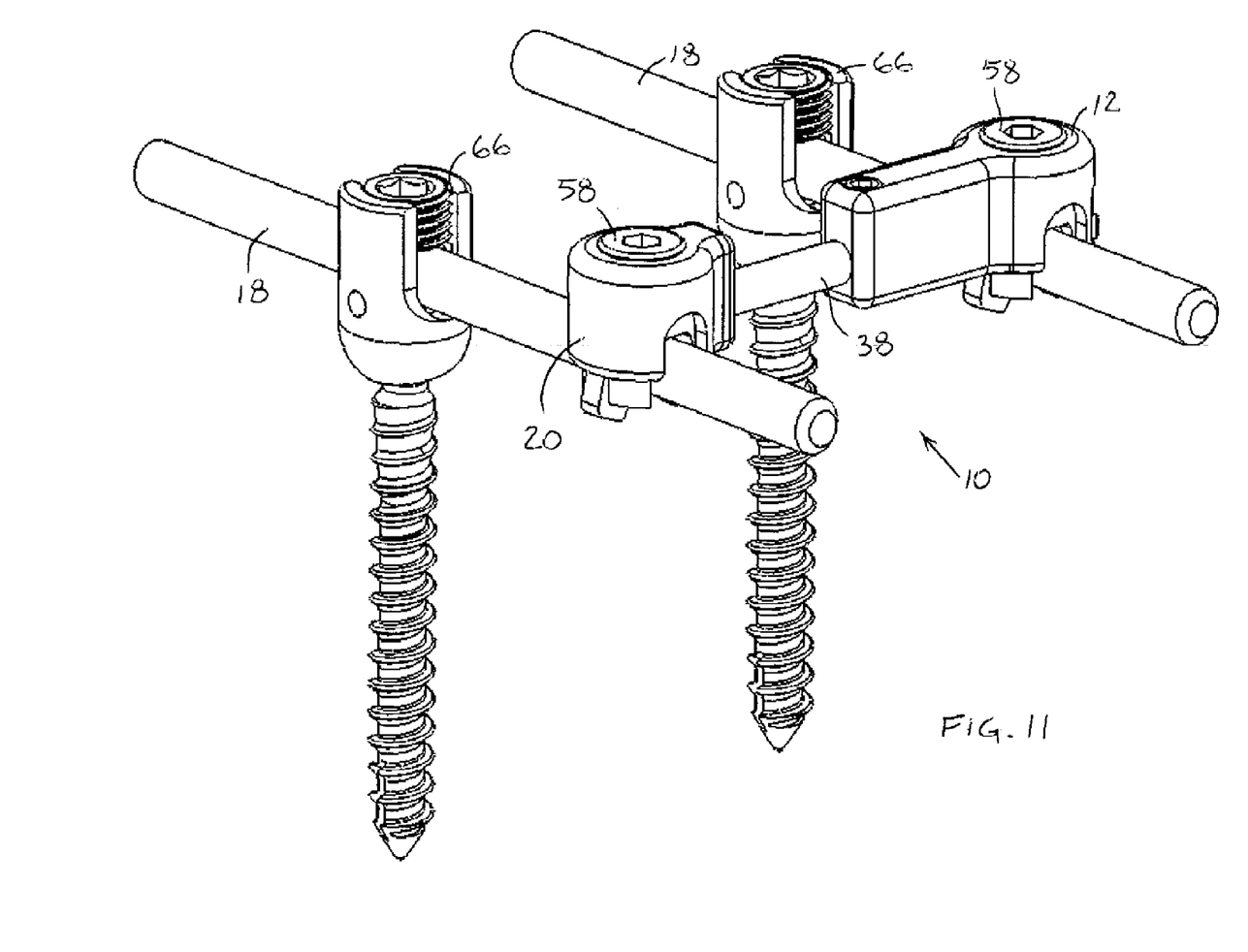
FIG. 11 is a simplified pictorial illustration of the cross-connector assembly connected to a connector rod and bone anchoring elements (pedicle screws), in accordance with an embodiment of the present invention.

Reference is now made to FIG. 11, which illustrates cross-connector assembly 10 connected to connector rods 18, which are connected to bone anchoring elements (pedicle screws) 66, in accordance with an embodiment of the present invention. The bone anchoring elements 66 may be threaded mechanical fasteners (for example, without limitation, a pedicle screw, a pedicle anchor device, a bone hook, a blocking screw for a pedicle anchoring device or any other device for attachment to the pedicle or others sections of the vertebral bone).

Figure 12:
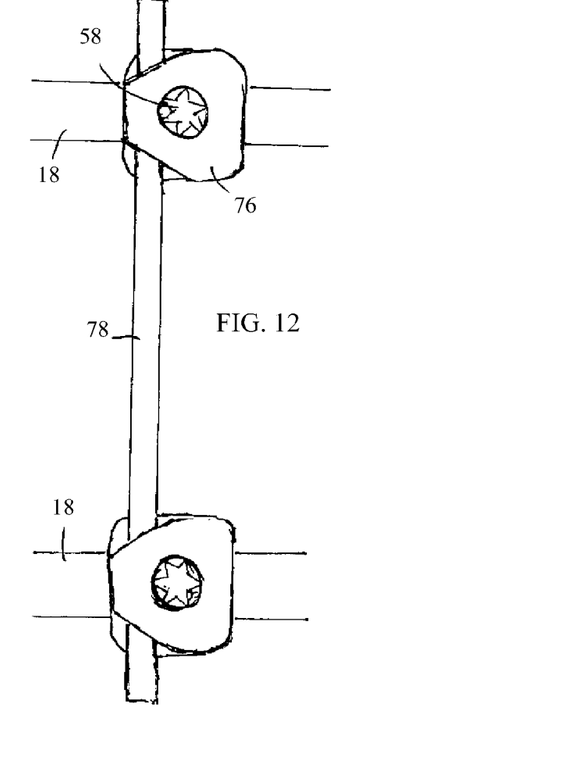
FIGS. 12, 13A and 13B are simplified pictorial and two partially-sectional illustrations, respectively, of a cross-connector assembly and connector element for a bone anchoring element, constructed and operative in accordance with another embodiment of the present invention.
Figure 13A:
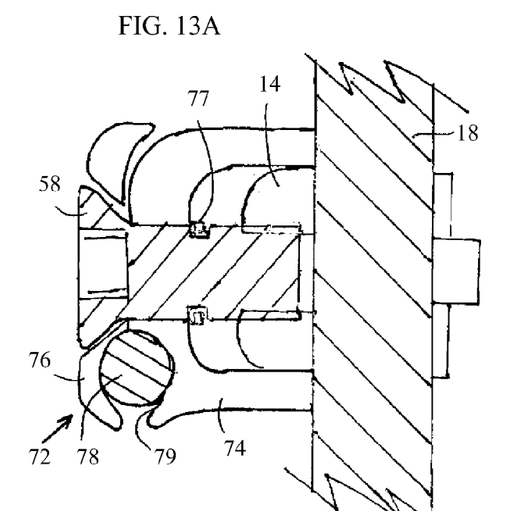
Figure 13B:
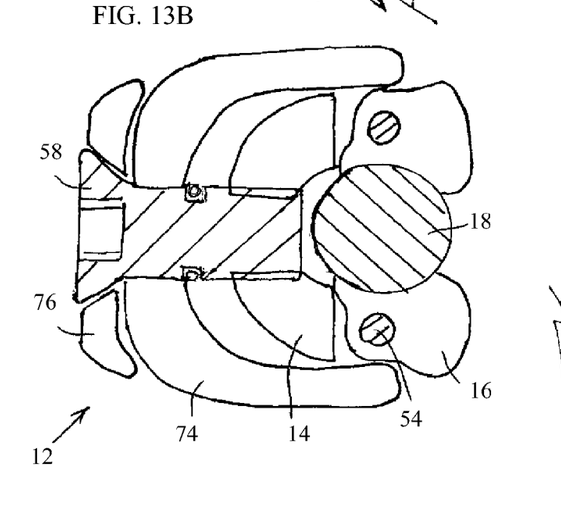

Reference is now made to FIGS. 12-13B, which illustrate a cross-connector assembly 70 and connector element 72 for a bone anchoring element, constructed and operative in accordance with another embodiment of the present invention. The connector element 72 of this embodiment is similar to the connector element 12 of cross-connector assembly 10, with like elements being designated by like numerals. Briefly, connector element 72 cooperates with lug element 14 and pivoting ears 16 that pivot about pivots 54 for gripping a connecting rod 18. Mechanical fastener 58 is screwed into tapped holes of a body 74 and lug element 14. This pulls lug element 14 towards the top portion of connector element 72, which causes the ears 16 to abut against the inner side walls of body 74. This causes the ears 16 to pivot about pins 54 and wrap against connector rod 18.

Figure 14:
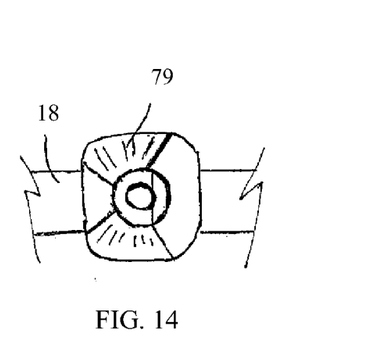
FIG. 14 is a simplified illustration of a recess in the connector element of the embodiment of FIGS. 12-13B, used to orient a cross bar or other anchoring element at different angular orientations.

In this embodiment, cross-connector assembly 70 further includes a washer cap 76 arranged to press against and hold a cross bar 78 or other anchoring element in a recess 79 formed in body 74. An O-ring 77 may be disposed on a portion of mechanical fastener 58 for preventing pull-out of fastener 58. The O-ring may be used in other embodiments of the invention as well. As seen in FIG. 14, the recess 79 may be fan-shaped to permit angular (e.g., azimuthal) adjustment of the cross bar or other anchoring element. Other fastening arrangements different from the recess 79 and washer cap 76 may be used to hold the cross bar and still permit angular adjustments. Accordingly, cross-connector assembly 70 can be used to hold connecting rods 18 and cross bar 78 at any desired spatial orientation.

It is important to note that in all the embodiments of the invention, the connector assembly can be used to grip not just a connecting rod but any bone-anchoring element. For example, the assembly can be used to directly grip and hold a pedicle screw connector, wherein the head of the screw is designed to fit in and be held by the ears 16 of the cross connector assembly. In this way, the screws are inserted first and then the cross connector is attached to the screw head (or hook or any other anchoring element).

Figures 15, 16:
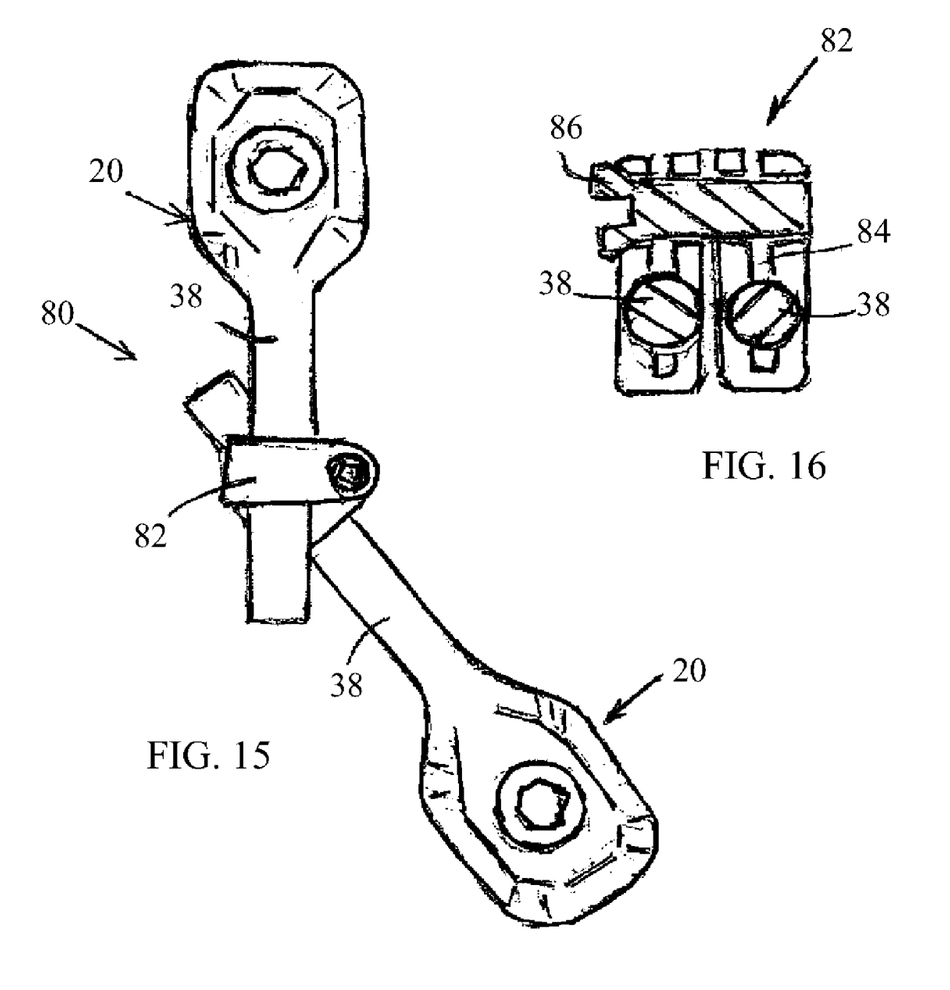
FIGS. 15 and 16 are simplified pictorial and sectional illustrations, respectively, of a cross-connector assembly for a bone anchoring element, constructed and operative in accordance with yet another embodiment of the present invention.

Reference is now made to FIGS. 15-16, which illustrate a cross-connector assembly 80 for a bone anchoring element, constructed and operative in accordance with yet another embodiment of the present invention. Cross-connector assembly 80 includes two transverse connector elements 20, instead of one transverse connector element 20 and one connector element 12. The transverse rods 38 of each transverse connector element 20 are linked by a hinged connector 82 that enables angled and telescopic relative movement between the transverse connector elements 20. As seen in FIG. 16, hinged connector 82 includes a plurality of resilient receptacles 84 for receiving therein transverse rods 38. The resilient receptacles 84 may be formed from titanium alloy or other suitable material. The resilient receptacles 84 may be formed as U-shaped channels whose sides are squeezed together by a mechanical fastener (e.g., screw) 86. Tightening mechanical fastener 86 grips the transverse rods 38 and locks them in a desired orientation.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. An assembly comprising:
   a connector element comprising a receptacle;
   a lug element sized to fit in said receptacle of said connector element;
   ears pivotally connected to said lug element;
   a mechanical fastener that fastens said connector element together with said lug element, wherein said lug element comprises a top surface formed with a hole and said receptacle comprises a hole formed on a top portion thereof, and said lug element is placed in said receptacle so that said hole of said lug element is aligned with said hole of said connector element, and said mechanical fastener is received in said holes, which causes said ears to abut against inner side walls of said connector element, thereby causing said ears to pivot and grip a bone anchoring element placed between said ears; and
   a transverse connector element that connects to said connector element in a telescoping manner.

2. The assembly according to claim 1, wherein a neck extends from said receptacle and wherein said transverse connector element comprises a receptacle from which extends a transverse rod that is received in said neck of said connector element in a telescoping manner.

3. The assembly according to claim 2, further comprising another lug element sized to fit in said receptacle of said transverse connector element, wherein ears are pivotally connected to said other lug element, and another mechanical fastener that fastens said transverse connector element together with said other lug element, thereby causing said ears to pivot and grip another bone anchoring element placed between said ears.

4. The assembly according to claim 3, wherein said bone anchoring elements are connected to other bone anchoring elements.

5. The assembly according to claim 1, wherein said receptacle of said connector element is formed with aligned U-shaped apertures on opposite side walls thereof, and a tapped hole on a top portion thereof.

6. The assembly according to claim 1, wherein a neck extends from said receptacle, and said neck is formed with a hole at an end thereof and a tapped hole on a top portion thereof.

7. The assembly according to claim 1, wherein said receptacle of said transverse connector element is formed with aligned U-shaped apertures on opposite side walls thereof, and a tapped hole on a top portion thereof.

8. The assembly according to claim 1, wherein legs extend from said top surface of said lug element, wherein said legs are formed with holes for pivotally pinning thereto said ears.

9. The assembly according to claim 1, wherein said lug element is pinned to said connector element with a pin passing through an angled hole formed in said lug element.

10. The assembly according to claim 1, wherein said lug element is pinned to said transverse connector element with a pin passing through an angled hole formed in said lug element.

11. The assembly according to claim 1, further comprising a washer cap arranged to press against and hold a bone anchoring element in a recess formed in a body of said connector element.

12. The assembly according to claim 11, wherein said recess permits angular adjustment of the bone anchoring element placed in said recess.

13. The assembly according to claim 1, further comprising a plurality of transverse connector elements connected to each other by a hinged connector.

14. The assembly according to claim 13, wherein said hinged connector enables angled and telescopic relative movement between said transverse connector elements.

* * * * *